United States Patent [19]

Klothen

[11] Patent Number: 4,824,829

[45] Date of Patent: Apr. 25, 1989

[54] NON-DUSTING ANTIBIOTIC, ANTICOCCIDIAL PREMIX COMPOSITIONS AND A PROCESS FOR THEIR MANUFACTURE

[75] Inventor: Irving Klothen, Princeton, N.J.

[73] Assignee: American Cyanamid Company, Stamford, Conn.

[21] Appl. No.: 750,144

[22] Filed: Jul. 2, 1985

Related U.S. Application Data

[63] Continuation-in-part of Ser. No. 641,094, Aug. 15, 1984, abandoned.

[51] Int. Cl.[4] .............................................. A61K 31/70

[52] U.S. Cl. ....................................... 514/27; 514/460

[58] Field of Search .................................. 514/27, 460

[56] References Cited

U.S. PATENT DOCUMENTS 4,211,781 7/1980 Chapman ............................ 514/249

4,278,663 7/1981 Liu et al. ............................ 424/121

OTHER PUBLICATIONS

*Formulation of Veterinary Dosage Forms,* Blodinger, Marcel Dekker, Inc., New York and Basel (1983) pp. 148–551, 158,159.

*Primary Examiner*—Frederick E. Waddell

*Attorney, Agent, or Firm*—John W. Hogan, Jr.

[57] ABSTRACT

The invention provides novel antibiotic, anticoccidial premix compositions which exhibit reduced dusting and lower dermal toxicities and a process for their manufacture.

9 Claims, No Drawings

NON-DUSTING ANTIBIOTIC, ANTICOCCIDIAL PREMIX COMPOSITIONS AND A PROCESS FOR THEIR MANUFACTURE

This application is a continuation-in-part of application Ser. No. 641,094 filed Aug. 15, 1984, now abandoned.

The invention relates to novel ionophore polyether antibiotic anticoccidial premix compositions comprising 0.25% to 35% on a weight basis of an ionophore polyether antibiotic, or a pharmaceutically or pharmacologically acceptable salt thereof, 0.75% to 35% of a physiologically acceptable alcohol such as benzyl alcohol, phenethyl alcohol and propylene glycol, 0.0% to 10.0% of a vegetable oil such as corn oil, or additional propylene glycol, and 30.00% to 99.00% of a sorptive, edible organic carrier such as corncob grits, extracted cornmeal, expanded corn grits, solvent extracted soybean meal, sorghum, or wheat middlings and the like or a sorptive silica or a silicate; process for the manufacture of such premix compositions and animal feed compositions containing the premix. The premix may be a solution of the ionophore polyether antibiotic anticoccidial and the alcohol.

Among the preferred ionophore polyether antibiotics for use in the compositions of the invention are monensin (structure I below), salinomycin (II), narasin (III), lasalocid (IV) and maduramicin (V) and the pharmaceutically and pharmacologically acceptable salts thereof.

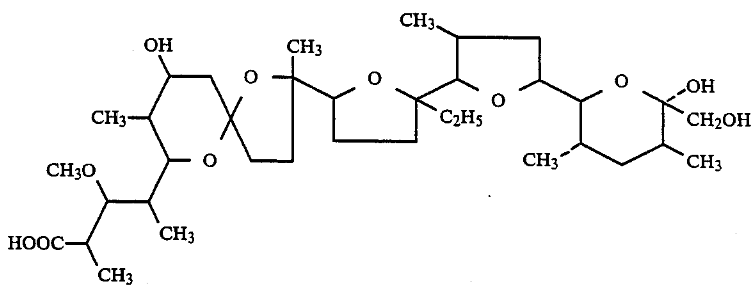

Monensin (I)

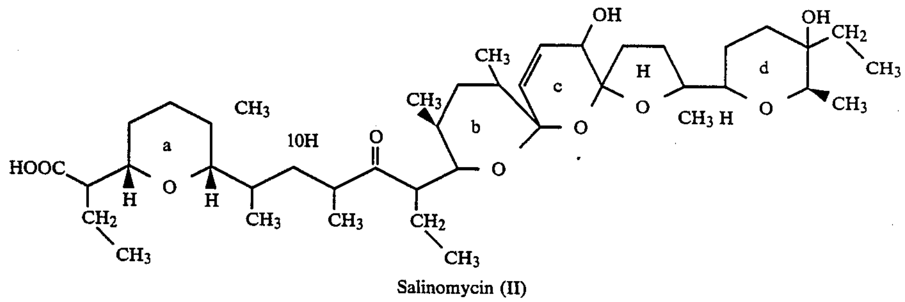

Salinomycin (II)

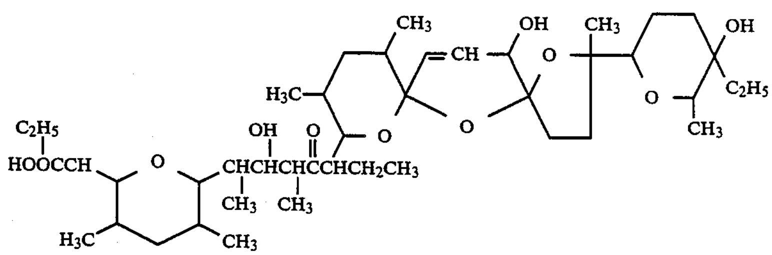

Narasin (III)

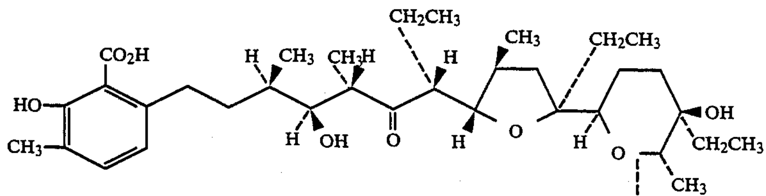

Lasalocid (IV)

-continued

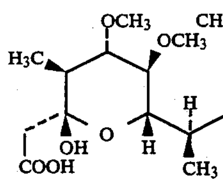

Maduramicin (V)

Antibiotics of structure (V) are disclosed in U.S. Pat. No. 4,278,663 and U.S. Pat. No. 4,368,265. These compounds are high effective anticoccidial agents and the drugs in their pure state are exceedingly toxic by physical contact, ingestion, and inhalation. Providing premixes which do not dust or segregate is highly desirable to minimize human contact with high concentrations of the drug and to help insure even distribution when the premix is mixed with animal feed.

Uniquely, it has been found that antibiotics of structures (I–V) may be applied to edible organic carriers as 10% to 35% solutions in physiologically acceptable alcohols such as benzyl alcohol and phenethyl alcohol and blended to give homogeneous animal feed premix compositions which exhibit reduced drug accumulation in dead spots upon blending into animal feed by as much as a seven-fold factor when compared to the same feed compositions prepared as dry mixes with pure drug as demonstrated in Table I below.

Table I represents a summary of the results obtained in Example # which is a segregation study comparing the use of dry pure drug and a premix composition of the invention.

TABLE I

| | Feed Prepared with Premix | | | Feed Prepared with Pure Drug | | |
|---|---|---|---|---|---|---|
| | Weight (g) | Assay (ppm) | Total Drug (mg) | Weight (g) | Assay (ppm) | Total Drug (mg) |
| #1 Neck accumulation | 1.82 | 1085 | 1.98 | 8.5 | 1745 | 14.8 |
| #2 Bulk sample | — | 935 | — | — | 1115 | — |
| #3 Bottle residue | 1.56 | 1800 | 2.81 | 0.80 | 2300 | 1.85 |

The results in Table I indicate that the pure drug when mixed dry with feed has a greater tendency to accumulate in the spots of least movement of processing equipment, the neck of the bottle in this test. Not only did a larger amount of feed accumulate in this spot when the drug was used instead of the 1% premix, 8.5 g vs 1.82 g, but the potency of the accumulated material was also much greater in the case of the pure drug, 1745 ppm vs 1085 ppm. Thus, the actual amount of drug segregating was more than seven times larger for pure drug than for premix. Such highly potent spots could cause toxicity, if ingested, would cause severe drug carry-over into following feed blends, and further indicate that the pure drug separates freely from the feed. This phenomenon could cause dusting problems of highly potent (and toxic) material presenting an inhalation and dermal hazard to operators. These difficulties are readily avoided by the use of a premix composition of the invention in animal feed compositions. The premix is incorporated into the feed by blending or mixing.

An additional advantage of handling ionophore polyether antibiotics as a solution in these alcohols is that solutions provide a safe and efficient way to handle materials in closed systems such as pipes and hoses during processing and formulations, avoiding the problems associated with handling solids during these procedures.

A further advantage of the compositions of the invention is that once formed, these premix compositions provide a significantly greater margin of safety in handling as illustrated in Table II below which shows the dermal toxicities of premix compositions of formula (I) antibiotic to be at least 100 times less than that of the pure drug or various solutions of the drug.

TABLE II

Relative Dermal Toxicities maduramicin

| | Composition | $LD_{50}$ Rabbit Dermal Toxicity Male mg/kg | Female mg/kg |
|---|---|---|---|
| 1. | Pure drug (92% pure) | 8.9 | 3.7 |
| 2. | Drug 24.8%<br>Benzyl alcohol 75.2% | 11.5 | 14.9 |
| 3. | Drug 13.0%<br>Benzyl alcohol 37.0%<br>Corn oil 50.0% | 37.9 | 17.3 |
| 4. | Invention Premix<br>Drug 1.0%<br>Benzyl alcohol 4.0%<br>Corn oil 5.0%<br>Corncob grits 90.0% | >4000 | >2000 |

The premix compositions of the invention may be readily prepared by dissolving the pure drug in a physiologically acceptable alcohol optionally diluted with a vegetable oil or additional propylene glycol and feeding the resulting mixture in a fine stream or spray onto the carrier while blending. The mixture is blended until homogeneous, resulting in a dry granular non-dusting premix. Alternatively, the premix compositions of the invention may be prepared from crude biomass material by extraction of the biomass into said physiologically acceptable alcohol and utilizing the alcohol extract directly in the preparation of the premix composition.

The invention is further illustrated by the following non-limiting examples.

EXAMPLE 1

Preparation of a premix composition

The ammonium salt of crude maduramicin (55 g, 1.1% on a weight basis) is dissolved in 385 g, 7.7% on a weight basis, of benzyl alcohol, forming a murky suspension. This suspension is fed in a fine stream into a ribbon blender (one cubic foot capacity) holding 4,460 g, 89.2% on a weight basis of granular corncob (Grit-O-Cob) and is followed by the addition of 100 g, 2.0% on a weight basis, oil as a rinse of the container. The mixture is allowed to blend until uniform, about ten minutes, and a freeflowing dry granular product results. HPLC assay of this mixture confirms the formula at 0.99%.

EXAMPLE 2

Preparation of premix compositions of ionophore polyether antibiotics

A. The pure drug or salt thereof is dissolved in the appropriate alcohol and optionally diluted with a vegetable oil or additional propylene glycol. The resulting solution is introduced onto the desired carrier and the mixture is blended until it is homogeneous.

B. Biomass material containing an antibiotic is extracted with physiologically acceptable alcohol such as benzyl alcohol, phenethyl alcohol or propylene glycol. Filtration yields an alcohol solution containing the antibiotic which is assayed for drug content. The desired quantity of the solution is then blended onto a carrier and the mixture blended until it is homogeneous. Utilizing these procedures yields the premix compositions listed in Table III below.

TABLE III

| | Premix compositions of ionophore polyether antibiotics | grams | |
|---|---|---|---|
| 1. | Monesin sodium (93%) | 4.3 | |
| | Benzyl alcohol | 11.7 | |
| | 25% Monesin Solution | 16.0 | |
| 2. | 25% Monesin solution | 4.0 | |
| | Corn cob grits 40/60 mesh | 26.0 | |
| | 3.33% Monesin premix | 30.0 | |
| | This dry premix is useful at 6 lb/ton of feed to supply 90 g of monesin per ton of feed when mixed into a complete feed. | | |
| 3. | 25% Monesin Solution | 5.2 | |
| | Fumed silica | 1.8 | |
| | 20% Monesin premix | 7.0 | |
| | This dry premix is useful at 1 lb/ton to supply 90 g monesin per ton of feed when mixed into a complete feed. | | |
| 4. | 25% Monesin solution | 2.0 | |
| | Expanded corn grits, 30 mesh | 3.0 | |
| | 10% Monesin premix | 5.0 | |
| | This premix can be used at 2 lb/ton to supply 90 g monesin to a ton of feed when mixed into such feed. | | |
| 5. | Monesin biomass (10% active) | 100.0 | |
| | Benzyl alcohol | 75.0 | |
| | Monesin Extract (ca. 11% a.i.) | 85.0 | (Recovered 38) |
| | This extract could be analyzed, diluted to exactly 10% for instance and used directly to spray into mixed animal feed at the rate of 2 lb/ton to supply 90 g monesin per ton. | | |
| 6. | Monesin Extract 11% | 5.0 | |
| | Fumed silica | 2.0 | |
| | Monesin premix 7.8% | 7.0 | |
| | This premix can be used at 2.5 g/ton to supply 90 g monesin. | | |
| 7. | Monesin biomass 25% active | 5.0 | |
| | Benzyl alcohol | 5.0 | |
| | Monesin extract 20% | 6.25 | (Recovered 3) |
| 8. | Monesin extract 20% | 2.0 | |
| | Corn cob grits | 11.33 | |
| | Monesin Premix 3% | 13.3 | |
| | This premix can be used at 9 lb/ton to supply 120 g monesin. | | |
| 9. | Monesin extract 11% | 15.0 | |
| | Hi-Sil (silica) | 7.0 | |
| | Monesin premix 7.5% | 22.0 | |
| 10. | Salinomycin sodium 100% | 0.22 | |
| | Benzyl alcohol | 0.20 | |

TABLE III-continued

| | Premix compositions of ionophore polyether antibiotics | grams | |
|---|---|---|---|
| | Salinomycin solution 52.4% | 0.42 | |
| | Corn cob grits 40/60 mesh | 2.91 | |
| | Salinomycin premix 6.6% | 3.33 | |
| | Two pounds of this premix supply 60 g salinomycin to medicate a ton of feed. | | |
| 11. | Salinomycin sodium 100% | 0.085 | |
| | Propylene glycol SUP | 0.100 | |
| | Salinomycin solution 46% | 0.185 | |
| | Propylene glycol USP | 0.015 | |
| | Corn cob grits | 1.100 | |
| | Salinomycin premix 6.5% | 1.300 | |
| 12. | Salinomycin biomass 5.5% a.i. | 100.0 | |
| | Benzyl alcohol | 75.0 | |
| | Salinomycin extract ca. 8% | 82.0 | (Recovered 50.5) |
| 13. | Salinomycin extract 8% | 6.5 | |
| | Verxite (mixed silicates) | 10.3 | |
| | Salinomycin premix 4.3% | 16.8 | |
| | This free-flowing premix can be used at 3 lb/ton to supply 60 g salinomycin to a ton of feed. | | |
| 14. | Narasin biomass (10% a.i.) | 50.0 | |
| | Benzyl alcohol | 25.0 | |
| | Narasin extract ca. 16.5% | 30.0 | (recovered 13.5) |
| 15. | Lasalocid sodium | 0.11 | |
| | Benzyl alcohol | 0.61 | |
| | Propylene glycol | 0.20 | |
| | Lasalocid solution 12% | 0.92 | |

It should be evident to those versed in the art that these examples are not to be thought of as limiting the applicability to the proportions shown. In particular, various techniques can be used to increase the concentration of active ingredient in the examples using biomass materials be refluxing or by use of more concentrated biomasses up to the limit of the solubility of the given ionophore antibiotic in the selected solvent.

EXAMPLE 3

Segregation study

The segregation test is performed in a commercially-blended poultry feed, supplemented with 1000 ppm (0.1%) of drug, using the premix prepared in Example 1 in one blend and pure drug with an equivalent amount of corncob grits in the other as indicated in Table IV below.

TABLE IV

| Component | A | B |
|---|---|---|
| 1% Premix (from Example 1) | 113.4 g | — |
| Pure technical drug | — | 1.26 g |
| Grit-O-Cob | — | 112 g |
| Poultry feed | 1026.6 g | 1029.7 g |

These materials are placed into new one-gallon Nalgene dense polyethylene jars and placed on a drum roller for two hours. At the end of the mixing time, the jars are sampled in the horizontal position to remove the material which has accumulated and packed in the neck (#1), then the jars are emptied without shaking or tapping, and a cross-sectional sample taken from the bulk (#2); finally, the empty jar is extracted and assayed for residual drug (#3).

The results of this experiment, which are summarized in Table V below, indicate that the pure drug (ca. 90% potency) when mixed dry with feed has a greater tendency to accumulate in the spots of least movement, the neck of the bottle in this test. Not only did a larger amount of feed accumulate in this spot when the drug was used instead of the 1% premix, 8.5 g vs 1.82 g, but the potency of the accumulated material was also much greater in the case of the pure drug, 1745 ppm vs 1085 ppm. Thus, the actual amount of drug segregating was more than seven times larger for pure drug than for premix. Such highly potent spots could cause toxicity, if ingested, would cause severe drug carry-over into following feed blends, and further indicate that the pure drug separates freely from the feed. This phenomenon could cause dusting problems of highly potent (and toxic) material presenting an inhalation and dermal hazard to operators. These difficulties are readily avoided by the use of a suitable premix such as the example cited here.

TABLE V

| | Sample A (Premix) | | | Sample B (Pure Drug) | | |
|---|---|---|---|---|---|---|
| | Weight (g) | Assay (ppm) | Total Drug (mg) | Weight (g) | Assay (ppm) | Total Drug (mg) |
| #1 Neck accumulation | 1.82 | 1085 | 1.98 | 8.5 | 1745 | 14.8 |
| #2 Bulk sample | — | 935 | — | — | 1115 | — |
| #3 Bottle residue | 1.56 | 1800 | 2.81 | 0.80 | 2300 | 1.85 |

EXAMPLE 4

Particle size and potency distribution of non-dusting premix compositions of the invention on different edible carriers Utilizing the procedure of Example 1, premix compositions containing 1% active ingredient are prepared using corncob grits or extracted cornmeal as the edible carrier. The particle size distribution is determined by standard sieve analysis, and the potency of drug within each particle size is determined by high performance liquid chromatography. The results of these experiments are summarized in Table VI below.

TABLE VI

| | One Percent Non-Dusting Premixes: Distribution by Size and Activity | | | | | |
|---|---|---|---|---|---|---|
| | PREMIX A | | | PREMIX B | | |
| Sieve Size (U.S.S.S. No.) | Amount % w/w | Average Potency % | Drug Distribution % of Total Drug | Amount % w/w | Average Potency % | Drug Distribution % of Total Drug |
| On 30 | 0 | 0 | 0 | 0.9 | 0.57 | 0.5 |
| On 30-100 | 99.8 | 0.98 | 99.7 | 97.3 | 0.92 | 95.8 |
| On 100-200 | 0.15 | 1.57 | 0.2 | 1.5 | 1.8 | 2.9 |
| Through 200 | 0.05 | 1.73 | 0.1 | 0.3 | 2.4 | 0.8 |

What is claimed is:

1. An antibiotic anticoccidial non-dusting dry feed premix composition comprising the following ingredients, all stated in terms of percentage of total weight of feed premix composition:
(a) 30.0% to 99.0% of a sorptive, edible organic carrier or a sorptive silica or a silicate on which has been sprayed and allowed to dry;
(b) a premix solution of 0.25% to 35% of an ionophore polyether antibiotic, or a pharmaceutically or pharmacologically acceptable salt thereof, 0.75% to 35% of a physiologically acceptable alcohol, provided that the ratio of said antibiotic or salt thereof to said alcohol is between about 1:10 and about 3:10, and 0.0% to 10.0% of a vegetable oil or additional physiologically acceptable alcohol.

2. A composition according to claim 1, wherein the antibiotic is monensin, salinomycin, narasin, lasalocid or maduramicin.

3. A composition according to claim 2 wherein the physiologically acceptable alcohol is benzyl alcohol, phenethyl alcohol and the vegetable oil is corn oil.

4. A composition according to claim 3 wherein the edible organic carrier is corncob grits, extracted cornmeal, expanded grits, soybean meal, sorghum, or wheat middlings.

5. A composition according to claim 4 wherein the antibiotic is the ammonium salt of maduramicin on a weight basis of 0.25% to 5% of the composition.

6. In an animal feed composition, the improvement which comprises incorporating therein a premix composition comprising 30% to 99% of a sorptive, edible organic carrier or a sorptive silica or a silicate on which has been sprayed and allowed to dry a solution of 0.25% to 35% on a weight basis of the premix composition of an ionophore polyether antibiotic or a pharmaceutically or pharmacologically acceptable salt thereof, 0.75% to 35% of a physiologically acceptable alcohol, provided that the ratio of said antibiotic to said alcohol is between about 1:10 and about 3:10, and 0.0% to 10% of a vegetable oil or additional physiologically acceptable alcohol.

7. A process for formulating a nondusting antibiotic anticoccidial composition comprising the steps of:
(a) dissolving an ionophore polyether antibiotic or a pharmaceutically or pharmacologically acceptable salt of an ionophore polyether antibiotic in a physiologically acceptable alcohol, provided that the ratio of said antibiotic to said alcohol is between about 1:10 and about 3:10 to form a solution;
(b) feeding the solution of step (a) onto 30.0% to 99% of a sorptive, edible carrier and
(c) blending the solution of step (a) and the carrier of step (b) into a uniform mixture allowing the solution of step (a) to dry to form a free-flowing, dry, granular composition.

8. A process according to claim 7 wherein the salt is the ammonium salt of the antibiotic maduramicin, the alcohol is benzyl alcohol, and the carrier is corncob grits.

9. The process of claim 8, wherein the benzyl alcohol is diluted with a vegetable oil or propylene glycol.

* * * * *